(12) United States Patent
Qureshi et al.

(10) Patent No.: US 10,001,115 B2
(45) Date of Patent: Jun. 19, 2018

(54) AIR SAMPLER WITH CLOSED LOOP FLOW CONTROL SYSTEM

(71) Applicant: IDEAL Industries, Inc., Sycamore, IL (US)

(72) Inventors: Aamir Qureshi, Huntingdonshire (GB); Stephen Tearle, Bedford (GB)

(73) Assignee: IDEAL Industries, Inc., Sycamore, IL (US)

(*) Notice: Subject to any disclaimer, the term of this patent is extended or adjusted under 35 U.S.C. 154(b) by 330 days.

(21) Appl. No.: 14/688,370

(22) Filed: Apr. 16, 2015

(65) Prior Publication Data

US 2016/0305415 A1 Oct. 20, 2016

(51) Int. Cl.
| | |
|---|---|
| *F04B 17/03* | (2006.01) |
| *F04B 49/06* | (2006.01) |
| *G05D 7/06* | (2006.01) |
| *G01N 1/22* | (2006.01) |
| *G01N 1/24* | (2006.01) |

(52) U.S. Cl.
CPC ............ *F04B 17/03* (2013.01); *F04B 49/06* (2013.01); *G01N 1/2273* (2013.01); *G01N 1/24* (2013.01); *G05D 7/0676* (2013.01); *G01N 2001/2276* (2013.01)

(58) Field of Classification Search
CPC ......... F04B 2203/0202; F04B 2205/05; G01N 1/2273; G01N 2001/2276
See application file for complete search history.

(56) References Cited

U.S. PATENT DOCUMENTS

| | | | |
|---|---|---|---|
| 4,292,574 A | 9/1981 | Sipin et al. | |
| 4,576,054 A | 3/1986 | Lalin | |
| 5,163,818 A | 11/1992 | Betsill et al. | |
| 5,520,517 A | 5/1996 | Sipin | |
| 5,553,508 A | 9/1996 | Dabberdt et al. | |
| 5,705,902 A | 1/1998 | Merritt et al. | |
| 6,167,766 B1 | 1/2001 | Dunn et al. | |
| 6,741,056 B1 | 5/2004 | Hall | |
| 7,336,045 B2 * | 2/2008 | Clermonts | H02P 6/06 318/400.07 |
| 7,347,112 B2 | 3/2008 | Kay | |

OTHER PUBLICATIONS

ISA/US, International Search Report and Written Opinion issued on PCT application No. US16/27272, dated Jul. 6, 2016, 18 pages.

* cited by examiner

*Primary Examiner* — Patrick Hamo
(74) *Attorney, Agent, or Firm* — Greenberg Traurig, LLP

(57) ABSTRACT

A battery powered, personal air sampler is described which uses a closed loop control circuit to adjust the power that is delivered to an internal pump such that a stable and accurate flow rate is maintained independent of changes in inlet pressure due to filter loading. Furthermore, the described personal air sampler provides improved efficiency to the entire electronic and flow pumping system which, in turn functions to optimize the available battery run time of the device.

12 Claims, 3 Drawing Sheets

AIR SAMPLER WITH CLOSED LOOP FLOW CONTROL SYSTEM

BACKGROUND

Personal air samplers are battery powered and bodily worn devices that are used to assess a workers exposure to toxic dusts and gasses.

By way of example, U.S. Pat. No. 6,741,056, issued on May 25, 2004 and incorporated herein by reference in its entirety, describes a personal air sampler in which a constant flow of air is provided regardless of changes in the air flow path. This result is achieved by altering the pump speed as a function of the power taken by the pump. The characteristics of the pump are pre-calibrated to provide a constant that is used together with the square of the voltage appearing across the motor armature coils (applied voltage minus back Emf), which reflects the power currently used, to adjust the motor speed and thus provide a constant flow of air under changing conditions of resistance.

By way of further example, U.S. Pat. No. 4,292,574, issued on Sep. 29, 1981 and incorporated herein by reference in its entirety, describes a personal air sampler with an electric motor that is driven by intermittent full-power pulses. More particularly, a constant selected running speed of the electric motor, with a varying mechanical load, is achieved by intermittently pulsing the motor at full power and comparing the back EMF of the motor, between power pulses, with a selected speed voltage, to accordingly control application of the power pulses. A particular control circuit is therefore described which permits operation of a pocket-sized system, powered by a three cell battery, to achieve substantially constant speed, at normally varying loads, throughout a ten hour period, with back EMFs at selected values between 0.01 volt (motor barely turning) and 2.0 volts (high speed).

While these described personal air samplers work for their intended purpose, the following describes an improved personal air sampler having a high efficiency closed loop control system.

SUMMARY

Generally, a battery powered, personal air sampler is described which uses a closed loop control circuit to adjust the power that is delivered to an internal pump such that a stable and accurate flow rate is maintained independent of changes in inlet pressure due to filter loading. The described personal air sampler thus provides improved efficiency to the entire electronic and flow pumping system which, in turn functions to optimize the available battery run time of the device.

More particularly, a personal air sampler is described that has a housing, the housing having an air inlet and an air outlet which defines an air flow passage. A pump is disposed in the air flow passage and functions to move air through the air flow passage at an air flow rate while a pressure sensing sub-system generates a signal indicative of the air flow rate. The sampling of the air flow rate may be performed continuously or at discrete, desired periods of time. A coreless DC motor drives the pump and a battery provides a voltage to the DC coreless motor. A regulator sub-system, having a switch and an inductor, is electrically coupled to and disposed between the battery and the coreless DC motor and a processing device is coupled to the regulator sub-system. A memory associated with the processing device has stored therein a look-up table for use in implementing a proportional-integrated-derivative closed loop air flow control process whereby the processing device is used to switch on and off the switch of the regulator sub-system as a function of the signal indicative of the air flow rate and data contained within the look-up table to thereby adjust the voltage that is provided from the battery to the coreless DC motor via the inductor in accordance with the proportional-integrated-derivative closed loop air flow control process whereupon a driving of the pump by the coreless DC motor is controlled for the purpose of having the air flow rate attain a target set point level.

A better understanding of the objects, advantages, features, properties and relationships of the described personal air sampler will be obtained from the following detailed description and accompanying drawing that set forth illustrative embodiments that are indicative of the various ways in which the principles expressed hereinafter may be employed.

BRIEF DESCRIPTION OF THE DRAWINGS

For a better understanding of the personal air samplers described hereinafter, reference may be had to preferred embodiments shown in the following drawings in which.

DETAILED DESCRIPTION

With reference to the figures, exemplary personal air samplers are now described. Generally, the described personal air samplers are battery powered devices that use a closed loop control circuit to adjust the power that is delivered to an internal pump such that a stable and accurate flow rate is maintained independent of changes in inlet pressure due to filter loading. Furthermore, the described personal air samplers provide improved efficiency to the electronic drive and flow pumping system which, in turn functions to optimize the available battery run time and size of the device.

Figure 1:
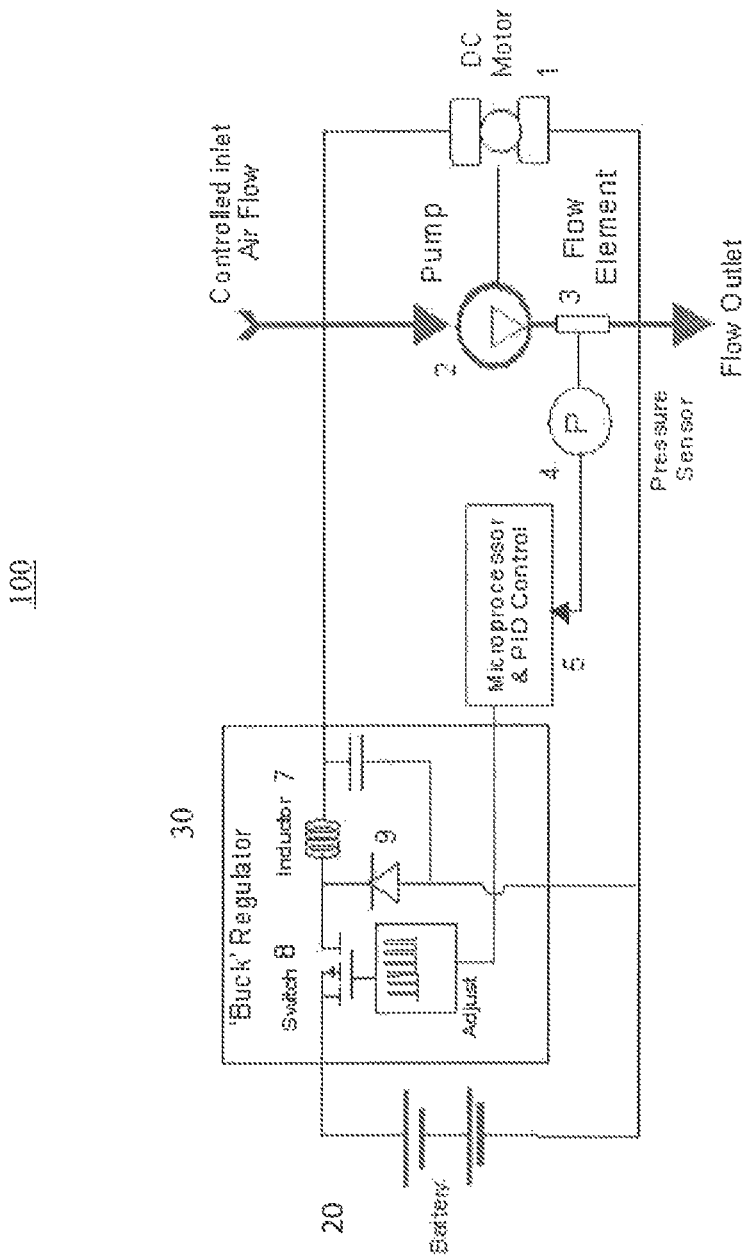
FIG. 1 is a block diagram illustrating an exemplary air sampler in Buck configuration.

As illustrated in FIG. 1, an exemplary personal air sampler 100 includes a battery for providing power to a DC motor 1. The DC motor 1 is, in turn, used to drive a pump 2 which is disposed between an air inlet of a housing of the personal air sampler 100 and an air outlet of the housing of the personal air sampler 100. In a preferred embodiment, the DC motor 1 is a coreless DC motor (typically 22 mm diameter and rated at between 6-12V and 5 W) and the pump 2 is a rotatory diaphragm pump. Further disposed within the air flow passage defined between the air inlet of the housing of the personal air sampler 100 and the air outlet of the housing of the personal air sampler 100 is a flow element 3. The flow element 3 is used to create a pressure signal that is proportional to the flow rate that passes through the pump 2 which, in turn, is measured by a pressure sensor 4. A signal indicative of the sensed pressure is provided from the pressure sensor 4 to a processing device 5. The processing device 5 has an associated memory in which is stored instructions for execution by the processing device 5 as well as a lookup table. Thus, the exact relationship between flow rate and the pressure signal may be determined by calibration which is retained within the lookup table. As will be appreciated, the memory may be included as a component part of the processing device 5 or may be one or more memory devices that are external to the processing device 5 as desired.

As further illustrated in FIG. 1, the exemplary personal air sampler 100 additionally includes a regulator sub-system 30 in the form of a buck regulator. Generally, a buck regulator includes an inductor 7 and the current in the inductor 7 is controlled by the use of a transistor switch 8 and a diode 9. In an idealized circuit, the components are considered "perfect" when the switch 8 and the diode 9 have zero voltage drop when on and zero current flow when off and the inductor 7 has zero series resistance. Recognizing the non-linear inductance characteristics of the DC coreless motor 1 with reduced inductance and saturation at higher current flow (because conduction losses depend on the inductive winding resistance of the motor and high switching currents in the motor winding resulting in high $I^2R$ losses), the regulator sub-system 30 uses the inductor 7 and the switch 8 and diode 9 to provide a high frequency and efficiency buck motor drive circuit. In particular, the addition of the discrete inductance in the motor drive functions to yield the advantage of increased drive efficiency. For example, it has been seen that the use of high drive frequencies (e.g., >40 kHz) and small inductance values (typically 6 to 40 uH) with low resistance yields high drive efficiencies (e.g., 85% or greater).

Figure 2:
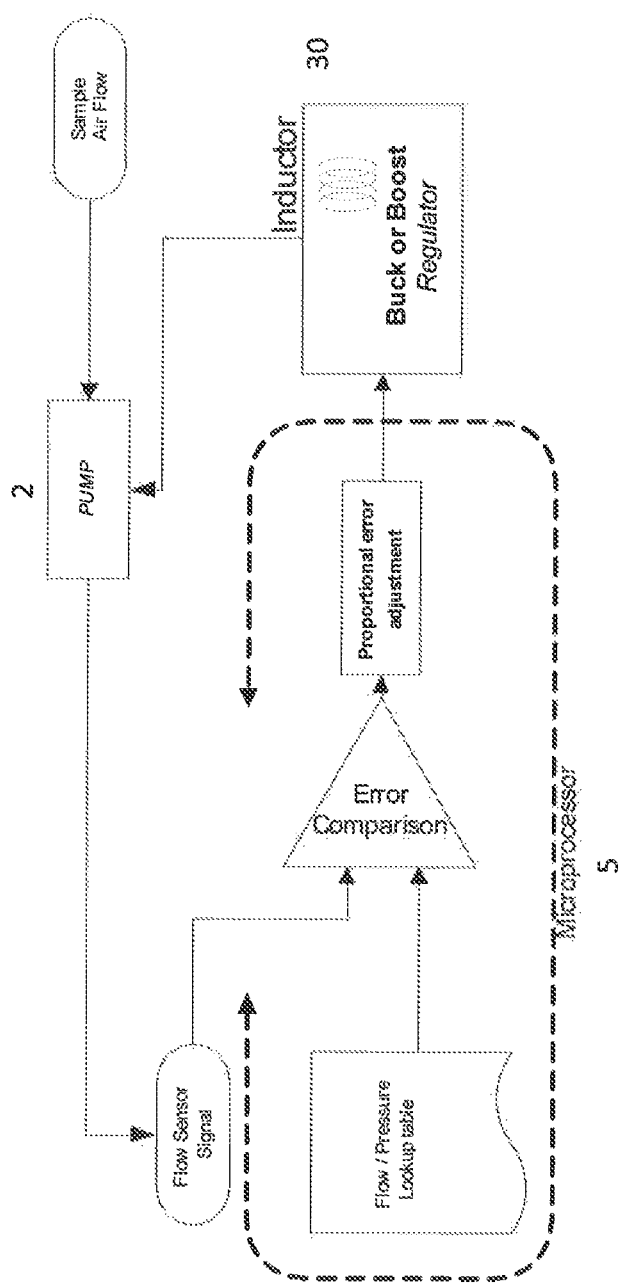
FIG. 2 is a flow diagram illustrating an exemplary method of operation for the air sample illustrated in FIG. 1.

In operation, for a specific flow rate, the target pressure value is determined using the lookup table as illustrated in FIG. 2. An error comparison of the target pressure value to the actual flow feedback pressure signal as provided to the processing device 5 by the pressure sensor 4 is used to establish the magnitude and direction of the flow error difference, i.e., the proportional error adjustment. To this end, a PID (proportional-integral-derivative) closed loop control algorithm is implement by the processing device 5. Specifically, mathematical constants within this PID control algorithm are preferably chosen to proportionally control the amount of change that is to be applied to the motor drive based upon the magnitude flow to set point error comparison. The control loop constants are therefore preferably optimized to achieve a fast response time whilst ensuring stability within the control system. Using such error comparison and proportional error adjustment, processing device 5 adjusts the output voltage of the regulator sub-system 30 which, in turn, adjusts the speed of the motor 1 and motor driven pump 2 such that the pressure sensor signal, and therefore the flow rate, is substantially maintained at the target set point level. In the exemplary embodiment, the high frequency switching drive of the regulator sub-system 30, e.g., the turning on and off of the switch 8, may be derived by using a discrete switching regulator or by using a pulse width modulation (PWM) or digital-to-analog signal provided directly by the processing device 5.

From the foregoing, it will be appreciated that the regulator sub-system 30 offers improved efficiency when stepping down the battery voltage to a lower level to drive the motor 1. As will also be appreciated, in the personal air sampling pump application the benefits of this increased efficiency are greatest at lower drive levels and midrange flow rates. For example, a 40% increase in the available run time has been demonstrated at a flow benchmark of 2 L/minute as compared to a system in which a conventional PWM drive is used using no additional inductance and lower switching frequencies.

Figure 3:
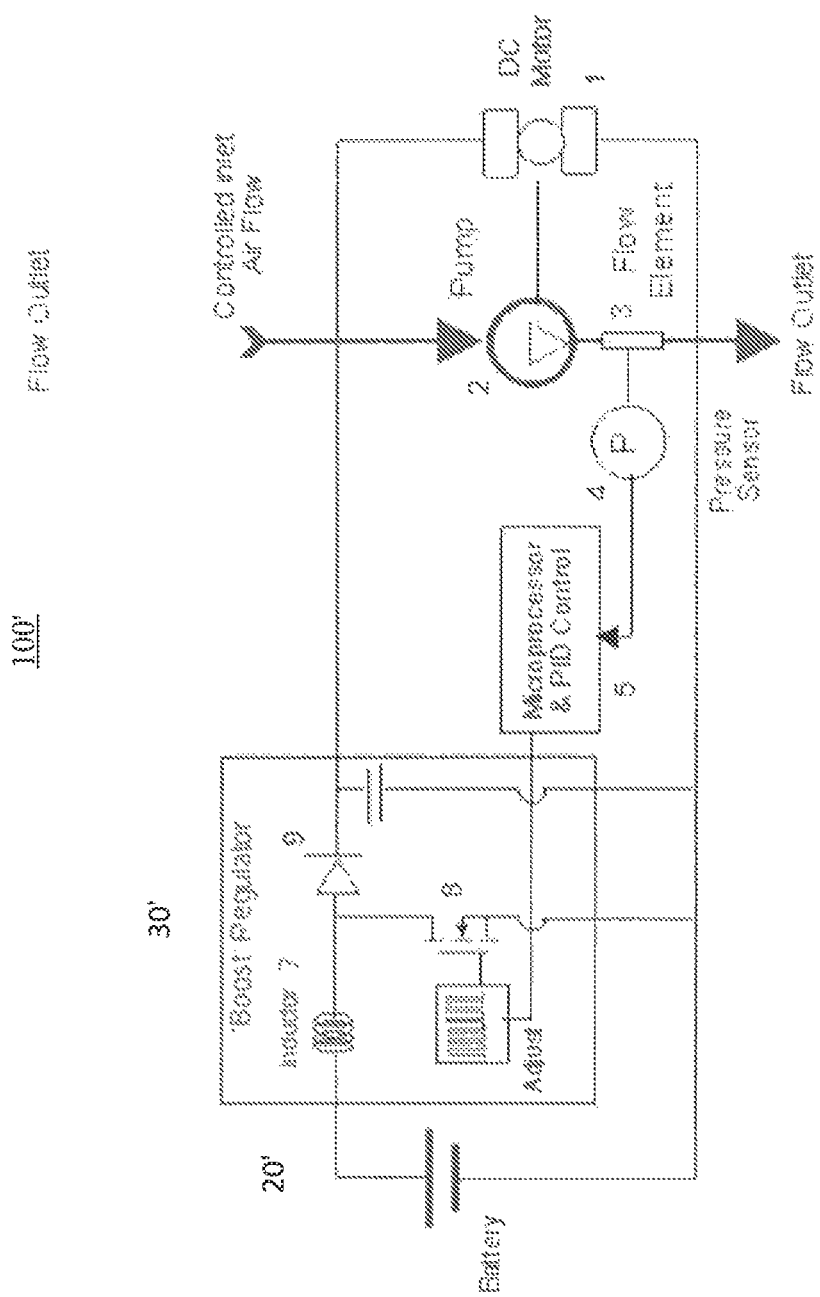
FIG. 3 is a block diagram illustrating a further exemplary air sampler in Boost configuration.

It is to be understood that the foregoing describes a system in which the regulator sub-system 30 is arranged to be used in a "step down" manner, i.e., arranged for use in a system in which the voltage of the battery 20 is greater than the maximum battery voltage that is required to drive the motor 1. For example, the system described and illustrated in FIG. 1 has been shown to provide efficiency gains when utilizing two Lithium Ion cells (nominal supply voltage of 7.2V) to drive a 5 L/min pump requiring a motor drive voltage less than 7.2 Volts. It is also to be understood that this arrangement is not intended to be limiting. Rather, it will be appreciated that a regulator sub-system 30', illustrated by way of example in FIG. 3, can be arranged to be used in a "step up" or boost manner with a battery 20'. To this end, the regulator sub-system 30' can be arranged in the form of a boost regulator whereby the additional inductance as described in this document is used to enable the provision of motor drive voltages that are higher than the available battery terminal voltage. In the air sampler 100' employing this regulator sub-system 30', and example of which is illustrated in FIG. 3, the added inductance 7 is placed between the battery 20' and the switching device 8 that is coupled to ground. When the switching device 8 is closed, current will flow through the inductor 7 and energy will be stored within its generated magnetic field and, when the switching device 8 is opened, the magnetic field of the inductor 7 will collapse producing a back emf across the inductor in a polarity such as to constructively add to the battery voltage. The combined battery and inductor emf will thus function to charge the capacitor through the diode 9. Again the inductor will be switched at a high frequency typically >20 khz and the switching modulation will form part of a closed control loop using a flow feedback sensing input as previously described, e.g., the processing device 5 may provide "adjustment" signals to the switch 8 to control this modulation as a function of the sensed flow rate and the data contained within the PID table. Accordingly, in this arrangement, a single lithium ion cell (3.6V) may be used to efficiently drive the pump 2 at voltages higher than the battery voltage and thus produce flow rates that would typically require the higher voltage that is provided by multiple series connected battery cells.

While specific embodiments of the invention have been described in detail, it will be appreciated by those skilled in the art that various modifications and alternatives to those details could be developed in light of the overall teachings of the disclosure. Accordingly, the particular arrangement disclosed is meant to be illustrative only and not limiting as to the scope of the invention which is to be given the full breadth of the appended claims and any equivalents thereof.

What is claimed is:

1. A personal air sampler, comprising:
  a housing having an air flow passage defined between an air inlet and an air outlet;
  a pump disposed in the air flow passage for moving air through the air flow passage at an air flow rate;
  a pressure sensing sub-system for generating a signal indicative of the air flow rate;
  a coreless DC motor for driving the pump;
  a battery for providing a voltage to the DC coreless motor;
  a regulator sub-system, having a switch and an inductor, wherein the switch is electrically coupled to and disposed between the battery and the inductor and the inductor is electrically coupled to and disposed between the switch and the coreless DC motor;
  a processing device coupled to the regulator sub-system; and a memory associated with the processing device having stored therein a look-up table for use in implementing a proportional-integrated-derivative closed loop air flow control process;

wherein the processing device switches on and off the switch of the regulator sub-system as a function of the signal indicative of the air flow rate and data contained within the look-up table to thereby adjust the voltage that is provided from the battery to the coreless DC motor via the inductor in accordance with the proportional-integrated-derivative closed loop air flow control process whereupon a driving of the pump by the coreless DC motor is controlled for the purpose of having the air flow rate attain a target set point level.

2. The personal air sampler as recited in claim 1, wherein the regulator sub-system is arranged to step-up the voltage that is provided from the battery to the DC coreless motor.

3. The personal air sampler as recited in claim 2, wherein the inductor of the regulator sub-system is arranged between the battery and the switch.

4. The personal air sampler as recited in claim 1, wherein the regulator sub-system is arranged to step-down the voltage that is provided from the battery to the DC coreless motor.

5. The personal air sampler as recited in claim 4, wherein the inductor of the regulator sub-system is arranged between the switch and the motor.

6. The personal air sampler as recited in claim 1, wherein the pressure sensing sub-system comprises a flow element for generating a pressure signal proportional to the flow rate and a pressure sensor which uses the pressure signal to generate the signal indicative of the air flow rate.

7. The personal air sampler as recited in claim 1, wherein the pump comprises a rotary diaphragm pump.

8. The personal air sampler as recited in claim 1, wherein the processing device uses a pulse-width-modulated signal to switch on and off the regulator sub-system.

9. A method for controlling an air flow rate through an air flow passage defined between an air inlet and an air outlet of a housing of a personal air sampler, the method comprising:

generating with a pressure sensing sub-system a signal indicative of a current air flow rate through the air flow passage;

using the signal indicative of the current air low rate through the air flow passage and data for use in implementing a proportional-integrated-derivative closed loop air flow control process as stored within a look-up table to control a regulator sub-system, having a switch and an inductor, wherein the switch is electrically coupled to and disposed between a battery and the inductor and the inductor is electrically coupled to and disposed between the switch and a coreless DC motor, whereby the switch is controlled to turn on and off to thereby adjust a voltage that is provided from the battery to the coreless DC motor via the inductor in accordance with the a proportional-integrated-derivative closed loop air flow control process whereupon a driving of a pump disposed in the air flow passage by the coreless DC motor is controlled for the purpose of having the current air flow rate attain a target set point level.

10. The method as recited in claim 9, comprising using the regulator sub-system to step-up the voltage that is provided from the battery to the coreless DC motor.

11. The method as recited in claim 9, comprising using the regulator sub-system to step-down the voltage that is provided from the battery to the coreless DC motor.

12. The method as recited in claim 9, comprising using a pulse-width-modulated signal turn on and off the switch of the regulator sub-system.

* * * * *